United States Patent
Yang et al.

(12)

(10) Patent No.: US 10,632,165 B2
(45) Date of Patent: Apr. 28, 2020

(54) **BENEFICIAL EFFECT OF *BIDENS PILOSA* ON FAT DECREASE AND MUSCLE INCREASE**

(71) Applicant: Academia Sinica, Taipei (TW)

(72) Inventors: Wen-Chin Yang, Taichung County (TW); Lee-Tian Chang, Taichung (TW); Yu-Chuan Liang, Taipei (TW)

(73) Assignees: Academia Sinica, Taipei, Taiwain (CN); NATIONAL CHUNG HSING UNIVERSITY, Taichung, Taiwan (CN)

( * ) Notice: Subject to any disclaimer, the term of this patent is extended or adjusted under 35 U.S.C. 154(b) by 13 days.

(21) Appl. No.: 16/068,125

(22) PCT Filed: Jan. 11, 2017

(86) PCT No.: PCT/US2017/013073
§ 371 (c)(1),
(2) Date: Jul. 4, 2018

(87) PCT Pub. No.: WO2017/127272
PCT Pub. Date: Jul. 27, 2017

(65) Prior Publication Data
US 2019/0000904 A1    Jan. 3, 2019

Related U.S. Application Data

(60) Provisional application No. 62/279,836, filed on Jan. 18, 2016.

(51) Int. Cl.
*A61K 36/28* (2006.01)
*A61K 31/7028* (2006.01)
*A23K 20/105* (2016.01)
*A23L 33/105* (2016.01)
*A61P 3/04* (2006.01)

(52) U.S. Cl.
CPC .......... *A61K 36/28* (2013.01); *A23K 20/105* (2016.05); *A23L 33/105* (2016.08); *A61K 31/7028* (2013.01); *A61P 3/04* (2018.01); *A23V 2002/00* (2013.01)

(58) Field of Classification Search
CPC . A61K 36/28; A61K 31/7028; A61P 3/04–10; A23K 20/105; A23K 20/163; A23L 31/105; A23L 31/30
See application file for complete search history.

(56) References Cited

U.S. PATENT DOCUMENTS

| | | | |
|---|---|---|---|
| 2007/0053998 A1* | 3/2007 | Yang | A61K 36/28 424/725 |
| 2008/0207512 A1 | 8/2008 | Roth et al. | |
| 2011/0091447 A1* | 4/2011 | Dosch | A61K 38/2093 424/130.1 |
| 2011/0268702 A1 | 11/2011 | Yang | |
| 2012/0022039 A1 | 1/2012 | Schwink et al. | |
| 2015/0272975 A1 | 10/2015 | Yang et al. | |

OTHER PUBLICATIONS

Ubillas, R. et al "Antihyperglycemic acetylenic glucosides . . . " Planta Med., vol. 6, pp. 82-83. (Year: 2000).*
Han, J. et al "Immune regulation in obesity-associated adipose inflammation" J. Immunol., vol. 191, pp. 527-532. (Year: 2013).*
International Search Report for PCT/US2017/013073, dated Apr. 4, 2017.
Written Opinion of International Search Authority for PCT/US2017/013073, dated Apr. 4, 2017.

* cited by examiner

*Primary Examiner* — Leigh C Maier
(74) *Attorney, Agent, or Firm* — Hsiu-Ming Saunders; Intellectual Property Connections, Inc.

(57) ABSTRACT

A composition comprising a therapeutically effective amount of *Bidens pilosa* extract, or an active compound isolated from the *Bidens pilosa* extract for use in treating obesity, reducing body weight or body weight gain, and/or gaining muscle mass or muscle content in a subject in need thereof is disclosed. The composition is useful for reducing fat cell size and/or fat accumulation in the fat cell in a subject in need thereof. The composition may further comprises an animal feed. A polyacetylenic compound for use in treating obesity, gaining muscle mass or muscle content, and/or increasing lean tissue protein content in a subject in need thereof is also disclosed. In one embodiment, the polyacetylenic compound is cytopiloyne.

20 Claims, 7 Drawing Sheets

BENEFICIAL EFFECT OF *BIDENS PILOSA* ON FAT DECREASE AND MUSCLE INCREASE

REFERENCE TO RELATED APPLICATION

This application is a national stage application (under 35 U.S.C. 371) of PCT/US2017/013073 filed on 11 Jan. 2017, which claims priority to U.S. provisional application 62/279,836 filed on 18 Jan. 2016, all of which are herein incorporated by reference in their entireties.

FIELD OF THE INVENTION

The present invention relates generally to methods for decreasing fat and/or increasing lean tissue protein content, and more specifically to methods for treating obesity.

BACKGROUND OF THE INVENTION

In 2014, it was estimated that 1.9 billion people worldwide were overweight and more than 600 million people were obese. Intake of excess energy drives adipocyte hyperplasia and hypertrophy, leading to obesity. Chronic obesity-related complications such as diabetes, cardiovascular disease, immune disorders and cancer impose an economic burden on patients and nations.

Pharmaceutical approaches are commonly used to combat obesity in addition to diet control and physical exercise. Current drugs used in weight losses act on reduction of fat absorption, suppression of appetite and increase of fullness. Despite their efficacy, weight-loss drugs are often accompanied by undesirable side effects and cost-effectiveness concerns. *B. pilosa*, an Asteraceae plant, is commonly used as a potherb or herbal medicine globally. This plant and/or its polyynes have been demonstrated to treat diabetes and hypertension.

SUMMARY OF THE INVENTION

In one aspect, the invention relates to use of a composition comprising a therapeutically effective amount of *Bidens pilosa* extract, or an active compound isolated from the *Bidens pilosa* extract in the manufacture of a medicament for treating obesity, reducing body weight or body weight gain, and/or gaining muscle mass or muscle content in a subject in need thereof. Alternatively, the invention relates to a composition comprising a therapeutically effective amount of *Bidens pilosa* extract, or an active compound isolated from the *Bidens pilosa* extract for use in treating obesity, reducing body weight or body weight gain, and/or gaining muscle mass or muscle content in a subject in need thereof.

The invention also relates to a method for treating obesity, reducing body weight or body weight gain, reducing body fat content, increasing protein content of lean tissues, gaining muscle mass or muscle content, and/or reducing fat cell size and/or fat accumulation in the fat cell in a subject in need thereof, comprising administering to the subject in need thereof a therapeutically effective amount of *Bidens pilosa* extract, or an active compound isolated from the *Bidens pilosa* extract.

In one embodiment, the active compound is a polyacetylenic compound of formula (I):

wherein
$R_1$ is H or $CH_3$;
$R_2$ is monosaccharide;
$R_3$ is H or $COCH_2COOH$;
m=3 or 4;
n=0 or 1;
o=1 or 2; and
p=1 or 2.

In another embodiment, the polyacetylenic compound is selected from the group consisting of In another embodiment, the active compound is cytopiloyne.

In another aspect, the invention relates to use of a composition comprising a therapeutically effective amount of a polyacetylenic compound of formula (I):

wherein
$R_1$ is H or $CH_3$;
$R_2$ is monosaccharide;

$R_3$ is H or $COCH_2COOH$;

m=3 or 4;

n=0 or 1;

o=1 or 2; and p=1 or 2, in the manufacture of a medicament for treating obesity, reducing body weight or body weight gain, and/or gaining muscle mass or muscle content in a subject in need thereof.

In one embodiment, the subject is: (i) obese; or (ii) non-obese but in need of increasing the protein content of lean tissues.

In another embodiment, the subject is a non-diabetic.

In another embodiment, the subject does not have metabolic syndromes, or does not have hypertension.

In another embodiment, the subject is selected from the group consisting of humans, non-human mammals, birds, reptiles, fishes, and amphibians.

In another embodiment, the *Bidens pilosa* extract is in a form of powder.

In another embodiment, the composition is in the form of food, an animal feed material, or a medicine.

In another embodiment, the composition is in a dosage form selected from the group consisting of oral, capsule, suppository and parenteral.

In another embodiment, the medicament is at a dosage of no less than 0.001 mg/kg body weight of the subject in need thereof.

Further in another embodiment, the medicament is at a dosage of no less than 0.015 mg/kg body weight of the animal in need thereof.

Further in another embodiment, the composition comprises an animal feed and 0.5%-15% (w/w) of *Bidens pilosa*.

Yet in another embodiment, the treating obesity, reducing body weight or body weight gain does not involve reducing food intake in the subject in need thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 3 shows changes in body composition of male ob/ob mice fed with *B. pilosa*. Five weeks post-treatment, the mice from FIG. 2 were subjected to MRI analysis. Fat tissue (A), lean tissue (B) and body fluid (C) in relation to body mass were measured and the data are presented as mean f SEM. Student's t-test was used to compare the difference between control and treatment groups and P≥0.05 (NS) and P<0.05 (*) are shown.

FIG. 5 shows effect of cytopiloyne, an active compound of *B. pilosa*, on differentiation of pre-adipocytes. The MTT assay of 3T3-L1 adipocytes grown in the medium containing vehicle or cytopiloyne at the indicated concentration for 24 hr is shown (A). 3T3-L1 pre-adipocytes were initiated for differentiation with DMSO (vehicle) and a mixture of Dex, IBMX and insulin for 2 days (B). The differentiating cells were then incubated with vehicle (inducer), rosiglitazone (RSG) or different doses of cytopiloyne until complete differentiation occurred. Lipid droplets from all the cells were visualized by Oil-Red-O staining and examined by light microscopy (left panel). Scale bars=10 μm. Oil Red O inside the cells was extracted and quantified at 520 nm (right panel). Expression of PPAR-γ and C/EBPα in 3T3-L1 cells treated with inducer in the presence of rosiglitazone (RSG) or cytopiloyne was analyzed by Western blot (C). The relative expression level (REL) of aP2 and adiponectin in 3T3-L1 cells was measured using real-time PCR (D). Effect of cytopiloyne on differentiation of human SGBS cells. The cells were incubated with DMEM/F12 medium (vehicle) or differentiation medium for 3 days (E). The cells were then incubated with vehicle (inducer) and cytopiloyne (25 μM) until a complete differentiation. The cells were stained with Oil Red O and photographed. Scale bar=20 μm. (F) *B. pilosa* and its active compound, cytopiloyne, inhibit adipogenesis via the down-regulation of the expression of PPAR-γ and C/EBPα and their downstream molecules, adiponectin and aP2.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "alkyl" refers to a saturated, linear or branched, non-aromatic hydrocarbon moiety, such as $CH_3$, $—CH_2—$, or branched $(CH_3)_2CH_2—$. The term "alkenyl" refers to a linear or branched, non-aromatic hydrocarbon moiety having at least one double bond, such as $CH_2=CH—$, or $—CH=CH—$. The term "alkynyl" refers to a linear or branched, non-aromatic hydrocarbon moiety having a least one triple bond, such as $CH\equiv C—$ or $—C\equiv C—$. The term "cycloalkyl" refers to a saturated non-aromatic cyclic hydrocarbon moiety, such as cyclohexyl. The term "cycloalkenyl" refers to a non-aromatic, cyclic hydrocarbon moiety that contains at least one double bond in the ring, such as cyclohexenyl. The term "heterocycloalkyl" refers to a saturated non-aromatic, cyclic moiety having at least one ring heteroatom (e.g., O, N, or S), such as 4-tetrahydropyranyl. The term "heterocycloalkenyl" refers to a non-aromatic, cyclic moiety having at least one ring heteroatom and at least one double bond in the ring, such as pyranyl. The term "aryl" refers to a hydrocarbon moiety having at least one aromatic ring. Examples of aryl moieties include phenyl, phenylene, biphenyl, naphthyl, naphthylene, pyrenyl, anthryl, and phenanthryl. The term "heteroaryl" refers to a moiety having at least one aromatic ring which contains at least one heteroatom. Examples of heteroaryl moieties include furyl, furylene, fluorenyl, pyrrolyl, thienyl, oxazolyl, imidazolyl, thiazolyl, pyridyl, pyrimidinyl, quinazolinyl, isoquinolyl, and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties. Examples of substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, heteroarylamino, diheteroarylamino, $C_1$-$C_{10}$ alkylsulfony, arylsulfonyl, heteroarylsulfonyl, $C_1$-$C_{10}$ alkylsulfonamide, arylsulfonamide, heteroarylsulfonamide $C_1$-$C_{10}$ alkylimino, arylimino, $C_1$-$C_{10}$ alkylsulfonimino, alrylsulfonimino, hydroxyl, halo, thio, $C_1$-$C_{10}$ alkylthio, arylthio, aminothioacyl, amidino, guanidine, ureido, cyano, nitro, nitroso, azido, acyl, thioacyl, acyloxy, carboxyl, amido, carbamoyl, and carboxyl, and carboxylic ester. Examples of substituents on alkyl, alkenyl, and alkynyl include all of the above-recited substituents except $C_1$-$C_{10}$ alkyl, $C_2$-$C_{10}$ alkenyl, and $C_2$-$C_{10}$ alkynyl. Cycloalkyl, cycloalkenyl, heterocycloalkyl, heterocycloalkenyl, aryl, and heteroaryl can also be fused with each other.

An animal feed refers to food given to domestic livestock, and pet (companion animal) food.

The term "pure compound" used herein refers to a compound that has a purity of at least 80% (e.g., 95% or 99%).

The term "treating" or "treatment" refers to administration of an effective amount of *Bidens pilosa* or its phytochemicals (e.g., polyacetylenic compounds such as 2-β-D-glucopyranosyloxy-1-hydroxytrideca-5,7,9,11-tetrayne (cytopiloyne) to a subject, who has obesity, or a symptom, with the purpose to cure, alleviate, relieve, remedy, ameliorate, or minimize the symptoms of it.

As used herein, "effective amount" or "sufficient amount" of *Bidens pilosa* or a compound refers to an amount that may be therapeutically effective to enhance growth, and/or inhibit, prevent, or treat a symptom of a particular disease, disorder, condition, or side effect described herein. For example, "an effective amount" may refer to the amount that is required to confer a therapeutic or a desired effect on the treated subject. Effective doses will vary, as recognized by those skilled in the art, depending on route of administration, excipient usage, and the possibility of co-usage with other therapeutic treatment.

By 0.5%~15% (w/w) it meant that all ten-thousandth, thousandth, hundredth, tenth and integer unit amounts within the range are specifically disclosed as part of the invention. Thus, 0.5%, 0.6%, 0.7%, 0.8%, 0.9% and 1%, 2%, 3%, 4% . . . 13%, 14%, and 15% unit amounts are included as embodiments of this invention.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$HED = \text{animal dose in mg/kg} \times (\text{animal weight in kg/human weight in kg})^{0.33}.$$

Abbreviations: Cytopiloyne, 2-β-D-glucopyranosyloxy-1-hydroxytrideca-5,7,9,11-tetrayne; SGBS, Simpson-Golabi-Behmel syndrome; PPARγ, peroxisome proliferator activated receptor γ; C/EBPα, CCAAT/enhancer binding protein α; aP2, adipocyte Protein 2.

*B. pilosa* powder was prepared first. Then animal diets were formulated by mixing with different percentages of *B. pilosa* powder.

*Bidens pilosa* preparation. Such a preparation can be obtained by stirring pulverized *Bidens pilosa* plants in water at an elevated temperature (e.g., at 50° C. or 100° C.) to form a suspension, and collecting a supernatant of the suspension. The supernatant can be further extracted with an alcohol (e.g., n-butanol) to provide an enriched preparation. The *Bidens pilosa* preparation contains one or more of the polyacetylenic compounds of the just-mentioned formula (I). For example, it contains cytopiloyne:

The polyacetylenic compounds described above include the compounds themselves, as well as their salts, prodrugs, and solvates, if applicable. Such salts, for example, can be formed by interaction between a negatively charged substituent (e.g., carboxylate) on a polyacetylenic compound and a cation. Suitable cations include, but are not limited to, sodium ion, potassium ion, magnesium ion, calcium ion, and an ammonium cation (e.g., tetramethylammonium ion). Likewise, a positively charged substituent (e.g., amino) on a polyacetylenic compound can form a salt with a negatively charged counter ion. Suitable counter ions include, but are not limited to, chloride, bromide, iodide, sulfate, nitrate, phosphate, or acetate. Examples of prodrugs include esters and other pharmaceutically acceptable derivatives, which, upon administration to a subject, are capable of providing above compounds described above. A solvate refers to a complex formed between a polyacetylenic compound and a pharmaceutically acceptable solvent. Examples of pharmaceutically acceptable solvents include water, ethanol, isopropanol, n-butanol, ethyl acetate, and acetic acid.

The polyacetylenic compounds may contain one or more asymmetric centers or a non-aromatic double bond. Thus, they can occur as racemates and racemic mixtures, single enantiomers, individual diastereomers, diastereomeric mixtures, and cis- or trans-isomeric forms. All such isomeric forms are contemplated.

Polyacetylenic compounds (e.g., cytopiloyne) can be isolated from *Bidens pilosa*. Whole *Bidens pilosa* plants are first pulverized and then stirred in heated water. After removal of insoluble materials (e.g., by filtration, decantation, or centrifugation), the resultant supernatant is subjected to liquid chromatography (e.g., high-pressure liquid chromatography) or other suitable methods to afford pure polyacetylenic compounds. The pure compounds thus obtained can be further derivatized to provide a number of other polyacetylenic compounds of this invention (U.S. Pat. No. 7,763,285, and Kusano et al (JP 2004083463), all of which are incorporated herein by reference in their entireties).

The polyacetylenic compounds described above can also be prepared by conventional methods. Below are three reaction schemes illustrating synthetic routes to a polyacetylenic compound of this invention.

Scheme 1

Butane-1,2,4-triol (i) is reacted with acetone to form a protected 1,2,4-triol compound (ii), which can be readily transformed to an iodo derivative (iii). Compound (iii) is then reacted with ethynyltrimethylsilane, under a basic condition (e.g., n-BuLi), to give (4-(2,2-dimethyl-1,3-dioxolan-4-yl)but-1-ynyl)trimethylsilane (iv). Compound (iv) is subsequently treated with an acid (e.g., acetic acid), followed by a coupling reaction with 2-bromoglucopyranose to afford an adduct (v). Compound (v) can be further treated with potassium fluoride to afford 2-phenyl-4H-chromen-4-one (vi).

Scheme 2

1-Bromoprop-1-yne (vii) is reacted with ethynylmagnesium bromide to afford penta-1,3-diyne (viii), which is further converted to hepta-1,3,5-triyne (ix). Compound (ix) can be readily transformed to 1-iodohepta-1,3,5-triyne (x) under a basic condition (e.g., n-BuLi), followed by addition of an iodo compound (e.g., $I_2$).

Scheme 3 demonstrates a coupling reaction between an acetylene derivative (vi), obtained from Scheme 1, and 1-iodohepta-1,3,5-triyne (x), obtained from Scheme 2, to a tetrayne compound (xi). Removal of protecting groups affords a polyacetylenic compound, 2β-D-glucopyranosyloxy-1-hydroxytrideca-5,7,9,11-tetrayne, a compound of this invention.

Synthetic chemistry transformations useful in synthesizing applicable compounds are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

This invention features a method of administrating an effective amount of one of the above-described polyacetylenic compounds or a *Bidens pilosa* preparation containing such a compound to a subject in need thereof.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

*Bidens pilosa* plants were collected from the campus of Academia Sinica, Taiwan. Approximately 10 kg of cleaned and crushed plants, in their entirety, was refluxed in 40 L of water for two hours. After removal of aqueous phase, insoluble materials was again refluxed in 25 L of water for two hours. The combined aqueous solutions (approximately 65 L) were evaporated in vacuo to yield a residue, which was subsequently suspended in 1.0 L of water and extracted with 1.0 L of n-butanol for three times. The n-butanol fraction was first evaporated on a vacuum rotary evaporator under reduced pressure and then lyophilized to provide a crude product of cytopiloyne (37.7 g).

The crude product was subsequently chromatographed over a RP-18 silica gel column with a $CH_3OH/H_2O$ gradient solvent system to give sub-fractions BPB1, BPB2, BPB3, and BPB4. The BPB3 fraction, eluted by 70% $CH_3OH$, was further fractionated by semi-preparative HPLC using a $CH_3H/H_2O$ solvent system. Cytopiloyne was obtained and characterized by $^1H$ NMR and $^{13}C$ NMR.

$^1H$ NMR (500 MHz, $CDOD_3$) δ 1.78 (2H, q, J=6.8 Hz), 1.98 (3H, s), 2.58 (2H, t, J=6.8 Hz), 3.19 (1H, dd, J=9.1, 7.8 Hz), 3.30 (1H, m), 3.34 (1H, m), 3.59 (2H, m), 3.65 (1H, dd, J=12.0, 6.5 Hz), 3.75 (1H, p, J=6.8 Hz), 3.85 (1H, dd, J=12.0, 1.7 Hz), 4.32 (1H, d, J=7.8 Hz); $^{13}C$ NMR (125 MHz, $CDOD_3$) δ 3.8, 16.1, 31.4, 60.0, 60.9, 61.8, 62.4, 62.6, 64.9, 65.8, 66.2, 71.5, 75.2, 77.9, 81.6, 104.8.

Calculation of the percentage of *Bidens pilosa* powder (BPP) is as follows: *Bidens pilosa* powder weight/*Bidens pilosa* powder weight+basic animal feed=% of BPP.

Here, we investigated the effect of *B. pilosa* on food intake, fat content, body weight and/or adipocyte size in ICR and ob/ob mice. Further, we tested the effect of this plant on the expressional regulation of PPARγ and C/EBPα in adipose tissues. Additionally, we examined the effect of *B. pilosa* on blood biochemistry. Finally, we studied the action of cytopiloyne, one active polyyne of *B. pilosa*, on adipogenesis and regulation of PPARγ and C/EBPα gene expression in adipocytes.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Methods

Chemicals and Reagents.

Dexamethasone (Dex), insulin, isobutylmethylxanthine (IBMX), Oil Red O powder, rosiglitazone (RGS), sodium bicarbonate, methylthiazoletetrazolium (MTT), TWEEN® 20, isopropanol, formaldehyde, glutamine, glucose, sodium pyruvate, sodium bicarbonate, pantothenic acid, cortisol, triiodothyronine and other reagents were purchased from Sigma-Aldrich (St. Louis, Mo., USA). Penicillin/streptomycin solution, Dulbecco's Modified Eagle's Medium (DMEM) and fetal bovine serum (FBS) were obtained from Hyclone Laboratories, Inc. (Logan, Utah, USA) and Life Technologies Corp. (Grand Island, N.Y., USA). *B. pilosa* extract and cytopiloyne were produced in compliance to the good manufacturing practices guidelines. Quality control of cytopiloyne in each batch of *B. pilosa* extracts was conducted as previously described (Lai, B. Y. et al. (2015) *Evid. Based Complement. Alternat. Med.* 2015, 832314).

Animals and Diet.

Four-week-old ICR mice and male C57Bl/6J obese (ob/ob) mice were obtained from BioLASCO (Taipei, Taiwan) and the National Laboratory Animal Center (Taipei, Taiwan), respectively. Animals were housed in a 12 h light/dark cycle in controlled temperature (22±2° C.) and humidity (55±10%) in a specific pathogen-free animal facility. All mice gained ad libitum access to rodent diet and water for 1 week prior to the study and beyond. *B. pilosa* at the indicated doses was used in the study and the number of calories in the diet supplemented with *B. pilosa* was measured. The average body weight of the mice was 26.38 g-26.76 g.

Blood Biochemistry.

After coagulation, mouse sera were collected from the blood samples by centrifugation at 4,000×g for 30 min at 4° C., and were analyzed using a Fuji Dri-Chem 4000i analyzer (Tokyo, Japan). Biochemical parameters such as total cholesterol (TC), triacylglycerol (TG), uric acid (UA), high-density lipoprotein (HDL), very low-density lipoprotein (VLDL), alanine aminotransferase (ALT), aspartate aminotransferase (AST), albumin and creatinine were determined.

Analysis of Body Composition.

The carcasses of ICR mice were lyophilized for 48-h. The dried body mass ($M_{b,dry}$) of each mouse was recorded and body water content was determined by subtracting $M_{b,dry}$ from flushed body mass. The carcasses were ground using a Sorvall Omni-Mixer (Sorvall, Newtown, Conn. USA). Fat content was determined using the ether extraction method, and protein content was measured using a KJELTEC™ Auto Analyzer (FOSS, Laurel, Md., USA). The water, fat and protein contents were expressed as a percentage of flushed body mass. To determine the body composition in live ob/ob mice, magnetic resonance imaging (MRI) system (Minispec LF50. Bruker, Ettlingen, Germany) was used to measure fat, lean tissue, and free body fluid.

Histochemical Staining.

Brown, subcutaneous and visceral adipose tissues were collected from each group of ob/ob mice. All adipose samples were fixed with 10% formalin and dehydrated with a graded concentration of ethanol (70%, 80%, 90%, 95%, and 100%). After clearing in two changes of xylene, the samples were impregnated with molten paraffin wax, embedded and blocked out. After cutting, 4- to 5-μm sections of the tissues were stained with hematoxylin and eosin and photographed under a microscope.

Cell Culture and Adipogenesis.

Mouse pre-adipocytes (3T3-L1 cells, CL-173) were obtained from American Type Culture Collection (ATCC®, Manassas, Va., USA). Human Simpson-Golabi-Behmel syndrome (SGBS) cells were established from a patient with the Simpson-Golabi-Behmel syndrome. 3T3-L1 cells were maintained in DMEM medium containing 10% FBS, 4 mM glutamine, 4.5 g/L glucose, 1 mM sodium pyruvate, and 1.5 g/L sodium bicarbonate. The differentiation of 3T3-L1 cells into adipocytes was initiated by the addition of 10 μM Dex, 0.5 mM IBMX and 10 μg/mL insulin to the confluent cells for 2 days. The cells were then differentiated in medium containing 10 μg/mL insulin together with DMSO, rosiglitazone and cytopiloyne for an additional 8 to 10 days. The medium was changed every 2 days until the differentiation was complete. For SGBS cells, the cells were cultured in differentiation medium (DMEM/F12 medium containing penicillin/streptomycin, 33 μM biotin, 17 μM pantothenic acid, 0.01 mg/mL mg transferrin, 0.1 μM cortisol, 0.2 nM triiodothyronine, 20 nM human insulin, 0.25 μM Dex, 0.5 mM IBMX and 2 μM RGS) for the first 3 days and switched to the differentiation medium lacking RGS, IBMX and Dexs for an additional 7 to 9 days.

MTT Assay.

MTT assay was used to determine cell viability of adipocytes. The cells were grown in the presence of cytopiloyne at $6 \times 10^3$ cells/well in a 96-well plate. After removing medium, MTT dye at 0.5 mg/mL was added to each well and incubated at 37° C. After 4 h, DMSO (150 μL/well) was added to each well and incubated at 37° C. for additional 1 h. The plate was measured at 570 nm (signal) and 650 nm (reference) using a microplate reader (UVM340, Biochrom, UK).

Oil Red O Staining and Lipid Quantification.

The differentiated adipocytes were washed with phosphate-buffered saline (PBS) and fixed with 4% formaldehyde for 15 min. After washing with PBS, the cells were stained with 0.06% Oil Red O for 30 min. After 70% ethanol washing, the cells were photographed under a microscope. For lipid quantification, isopropanol was used to extract the intracellular oil red O, followed by measurement at 520 nm using a microplate reader.

Western Blot. Total lysates from adipocytes or adipose tissues were electrophoresed by sodium dodecyl sulfate polyacrylamide gel electrophoresis (SDS-PAGE) and transferred to nitrocellulose membrane, immunoblotted with the antibodies against PPARγ (1:2000), C/EBPα (1:1000), p85 (1:5000) and/or β-actin (1:5,000) and horseradish peroxidase (HRP)-conjugated goat anti-mouse IgG as secondary antibody. After developing with ECL substrate (GE Healthcare, UK), the membranes were detected using FLUO-RCHEM™ HD2 system (Bio-Techne, Minneapolis, Minn., USA).

Statistical Analysis.

The data are presented as mean±standard error of the mean (SEM). Student's t-test was used to compare the difference between two groups unless indicated otherwise. Comparisons between multiple groups were made with ANOVA. P values less than 0.05 were considered statistically significant.

Results

Long-Term Effect of *B. pilosa* on Body Weight, Biochemical and Hematological Parameters and Body Composition in ICR Mice.

Figure 1:
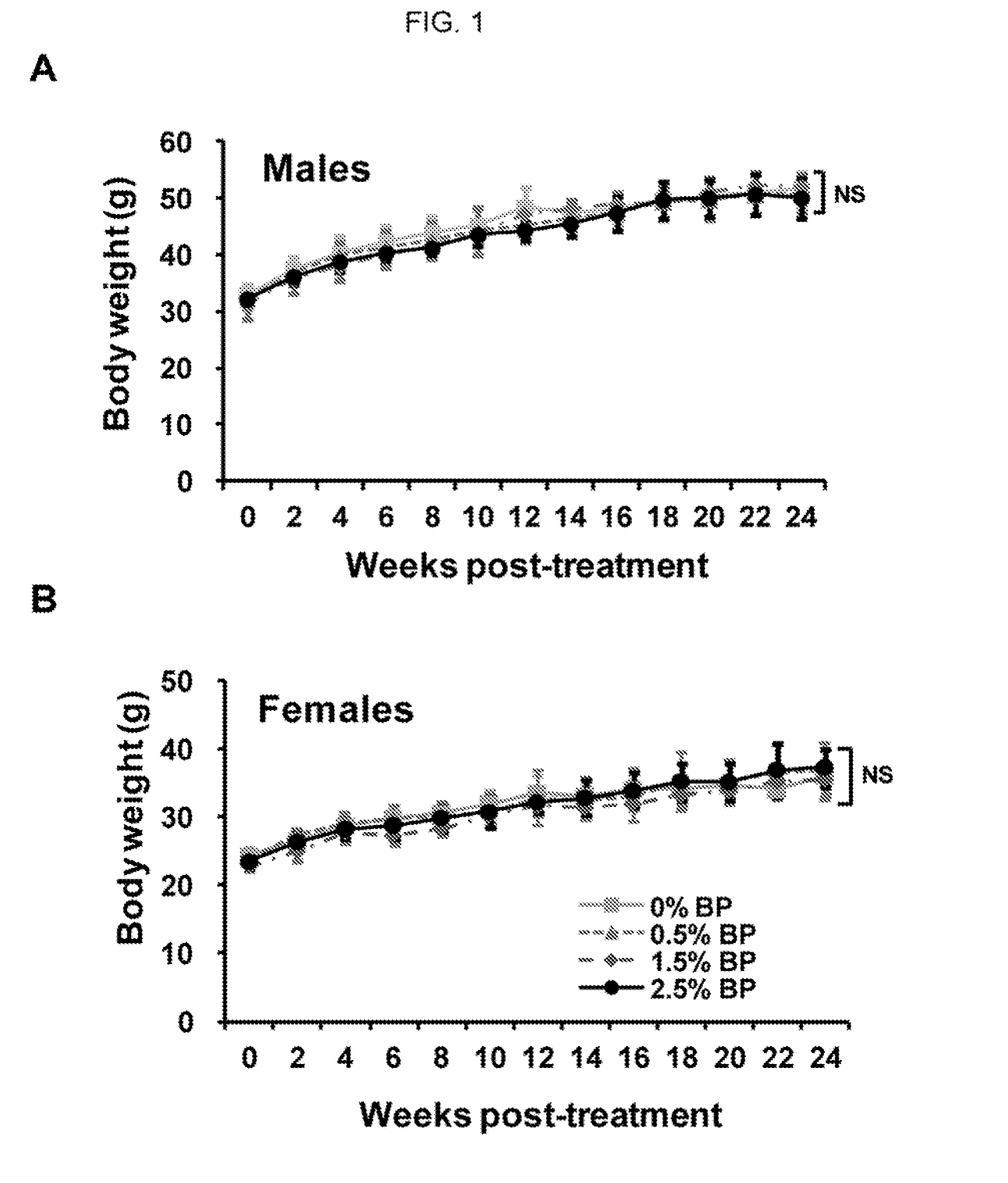
FIG. 1 shows changes of body weight in male (A) and female (B) ICR mice fed with *B. pilosa* for 24 weeks. All ICR mice, 5-week-old, were randomly assigned into 4 groups of males and 4 groups of females with 5 mice for each group. Each group were fed with a standard diet, a standard diet containing 0.5% *B. pilosa* extract (BP), 1.5% BP, or 2.5% BP for 24 weeks. Body weight in each group of mice was monitored before and after 24-week treatment. The data from each group are expressed as mean±SEM. Student's t-test was used to compare the difference between control and treatment groups and P values of greater than 0.05 (NS) are considered to be not significant.

To explore the anti-obesity effects of *B. pilosa*, we first assessed its long-term effect on body weight, body composition, serum biochemistry and hematology in ICR mice. ICR male (FIG. 1A) and female (FIG. 1B) mice were randomly assigned into 4 groups with 5 mice per group, and fed with a standard diet (0% BP), a standard diet containing 0.5% *B. pilosa* extract (BP), 1.5% BP, and 2.5% BP for 24 weeks, respectively. No significant difference (P≥0.05) in the body weight of ICR mice in either gender was observed before and after 24-wk treatment (FIG. 1A, 1B and Table 1). The food and water intake in control and *B. pilosa*-fed groups of male and female ICR mice were not statistically different (P≥0.05, data not shown). Body composition data showed that *B. pilosa* dependently reduced crude flit content in ICR females (Table 1). This reduction was more noticeable in males (Table 1). In addition, we also observed that *B. pilosa* dependently increased crude protein content in males to a greater extent than females (Table 1). Table 1 shows the effects of *B. pilosa* on body weight and composition of ICR mice.

TABLE 1

| | | | Body composition | |
|---|---|---|---|---|
| Groups | Initial BW (g) | Final BW (g) | Crude protein (%) | Crude fat (%) |
| Males | | | | |
| 0% BP | 32.9 ± 2.1 | 51.6 ± 3.0 | 14.2 ± 1.3 | 19.4 ± 2.0 |
| 0.5% BP | 32.3 ± 1.5 | 50.7 ± 3.1 | 15.3 ± 1.3* | 17.8 ± 3.1* |
| 1.5% BP | 31.2 ± 1.5 | 52.1 ± 2.3 | 19.6 ± 1.5** | 13.9 ± 2.2** |
| 2.5% BP | 32.2 ± 1.1 | 50.1 ± 3.6 | 19.3 ± 1.0** | 12.8 ± 1.7** |
| Females | | | | |
| 0% BP | 24.1 ± 1.4 | 36.1 ± 1.9 | 12.2 ± 1.1 | 22.8 ± 3.1 |
| 0.5% BP | 23.8 ± 1.3 | 36.8 ± 2.6 | 13.5 ± 1.7* | 20.5 ± 2.7* |
| 1.5% BP | 23.1 ± 0.9 | 36.5 ± 2.1 | 13.7 ± 1.8* | 18.6 ± 2.0* |
| 2.5% BP | 23.5 ± 1.0 | 37.3 ± 2.8 | 14.3 ± 1.5 | 16.5 ± 1.7** |

Four groups of 5-week-old ICR males and females were fed with a standard diet and standard diet containing 0.5% *B. pilosa* extract (BP), 1.5% BP, and 2.5% BP for 24 wk, respectively. Body weight and composition were measured. The body composition including crude protein and fat were calculated as percentages in the dried carcass mass. The data from 5 mice per group are expressed as mean±SEM. ANOVA was used to analyze the statistical significance. * P<0.05 and ** P<0.01 are considered to be statistically significant when compared with control group (0% BP).

We also examined the effect of *B. pilosa* on biochemical and hematological parameters in the mouse blood of each group. The variation in biochemical and hematological parameters between the control and *B. pilosa*-fed groups was observed. However, these parameters were indeed within normal range except that *B. pilosa* significantly lowered blood glucose in ICR females rather than males. The anti-diabetic property of *B. pilosa* was consistent with a previous study by Chien et al. (2009) ("Anti-diabetic properties of three common *Bidens pilosa* variants in Taiwan" *Phytochemistry* 70, 1246-1254). The results suggest the safety of *B. pilosa*. The data showed that *B. pilosa* had an impact on body composition in mice. Table 2 shows the effect of *B. pilosa* on serum chemistry in ob/ob mice.

TABLE 2

| Parameter | 0 week | | | 5 weeks | | |
|---|---|---|---|---|---|---|
| (mg/dL) | 0% BP | 0.5% BP | 2.5% BP | 0% BP | 0.5% BP | 2.5% BP |
| Glucose | 432.4 ± 15.9 | 56.8 ± 19.9 | 430.9 ± 16.5 | 627.4 ± 19.8 | 563.4 ± 12.1* | 537.3 ± 17.2* |
| Cholesterol | 149.2 ± 14.5 | 154.1 ± 15.3 | 62.3 ± 14.0 | 233.7 ± 15.7 | 161.0 ± 13.8* | 144.4 ± 12.6* |
| Triglyceride | 165.3 ± 9.7 | 173.8 ± 8.2 | 171.2 ± 7.6 | 338.5 ± 5.9 | 253.6 ± 1.4* | 231.6 ± 7.1* |
| Uric acid | 3.6 ± 0.3 | 3.1 ± 0.5 | 3.6 ± 0.1 | 4.7 ± 0.6 | 5.3 ± 0.1 | 5.1 ± 0.4 |
| HDL | 123.0 ± 2.2 | 120.7 ± 2.4 | 134.3 ± 3.4 | 148.7 ± 2.2 | 92.2 ± 1.0* | 83.2 ± 1.9* |
| VLDL | 38.1 ± 1.5 | 35.8 ± 1.7 | 36.2 ± 0.5 | 66.7 ± 1.2 | 50.7 ± 0.3* | 44.6 ± 1.7* |
| Insulin (μg/dL) | 0.35 ± 0.01 | 0.33 ± 0.01 | 0.34 ± 0.01 | 1.42 ± 0.04 | 0.95 ± 0.03* | 0.70 ± 0.02* |

Three groups of 5-week-old ob/ob mice were fed with a standard diet, a standard diet containing 0.5% *B. pilosa* extract (BP), or 2.5% BP for 5 wk. Serum samples from 5 mice per group were collected for biochemical analysis and the data are expressed as mean±SEM. * P<0.05 is considered to be statistically significant when compared with control group (0% BP).

*B. pilosa* Decreases Body Weight Gain and Fat Content but Increases Lean Tissue Content in ob/ob Mice.

Figure 2:
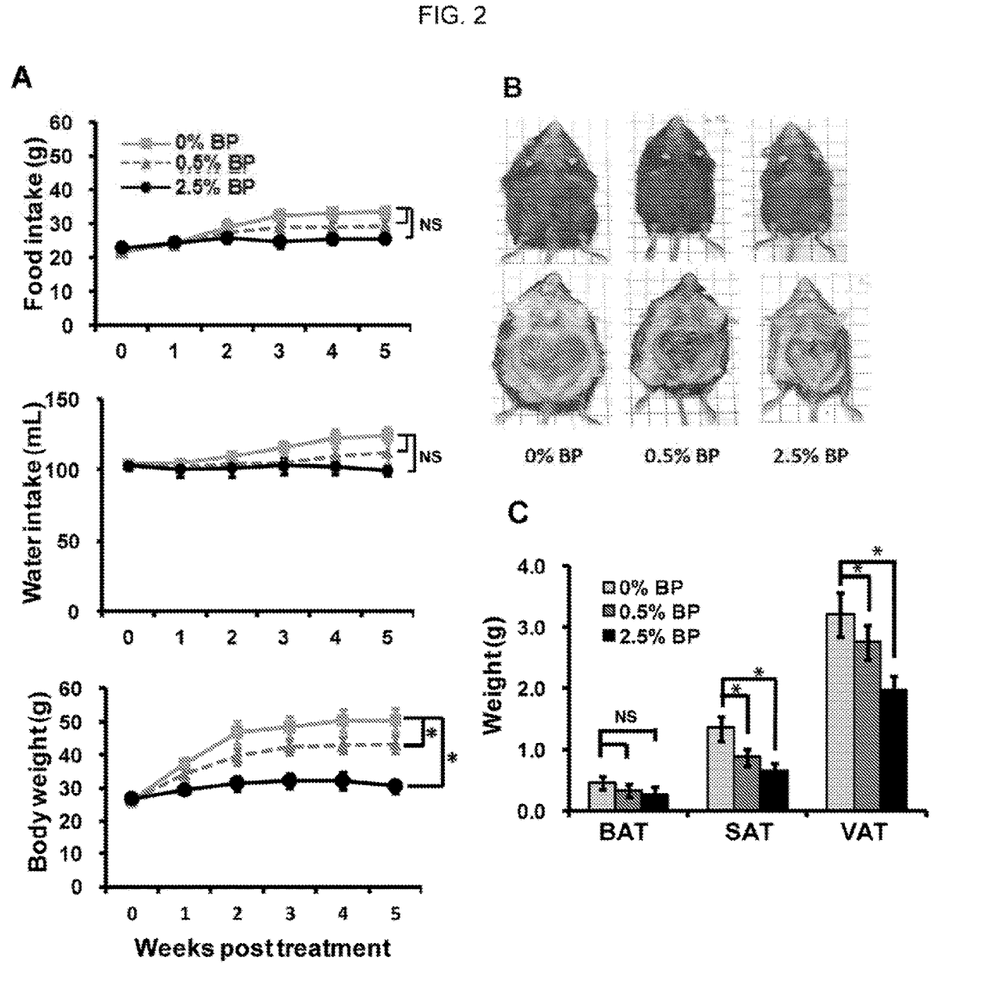
FIG. 2 shows changes in food consumption, water intake, body weight and fat tissues in male ob/ob mice fed with *B. pilosa*. (A) Three groups of 5-week-old mice fed with standard diet and standard diet containing 0.5% *B. pilosa* extract (BP) and 2.5% BP for 5 weeks. Food intake, water intake, and body weight were monitored weekly for 5 weeks. (B-C) The 10-week-old mice (B) and their adipose tissues (C) were photographed and weighed. Brown (BAT), subcutaneous (SAT) and visceral (VAT) adipose tissues are indicated. Student's t-test was used to compare the difference between control and treatment groups and P≥0.05 (NS) and P<0.05 (*) are shown.
Figure 3:
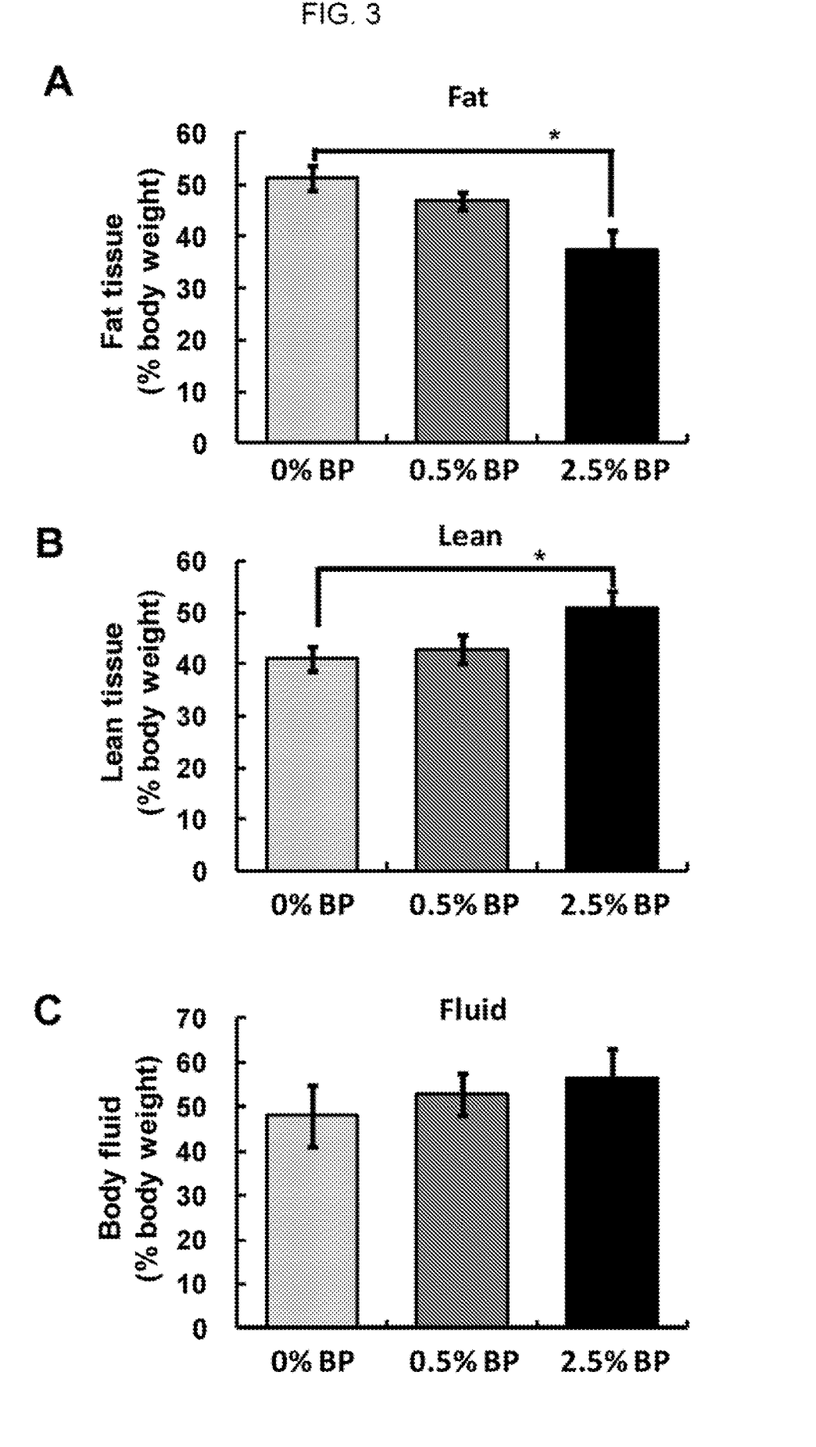

Next, the ob/ob mice, a mouse model of obesity, were used to further investigate the effect of *B. pilosa* on body weight and body composition. The 5-week-old males were randomly divided into 3 groups fed standard diet (0% BP) and standard diet containing low (0.5% BP) or high (2.5% BP) of *B. pilosa* extract for 5 weeks. No significant difference (P≥0.05) was observed in food and water consumption in the control and treatment groups of ob/ob mice (FIG. 2A). In contrast, *B. pilosa* dose-dependently decreased body weight (FIG. 2A) and fat (FIG. 2B). For adipose tissues, *B. pilosa* significantly diminished the weight of visceral and subcutaneous fat but not brown fat (FIG. 2C). Akin to the data in ICR mice, NMR data showed that *B. pilosa* decreased fat content in ob/ob mice in a dose-dependent manner (FIG. 3A). *B. pilosa* also increased the content of lean tissue in the mice (FIG. 3B). However, no difference (P≥0.05) in the body fluid between control and *B. pilosa*-fed mice was observed (FIG. 3B).

*B. pilosa* Reduces Cell Size and Expression Level of PPARγ and C/EBPα in Adipose Tissues of Obese Mice.

Figure 4A:
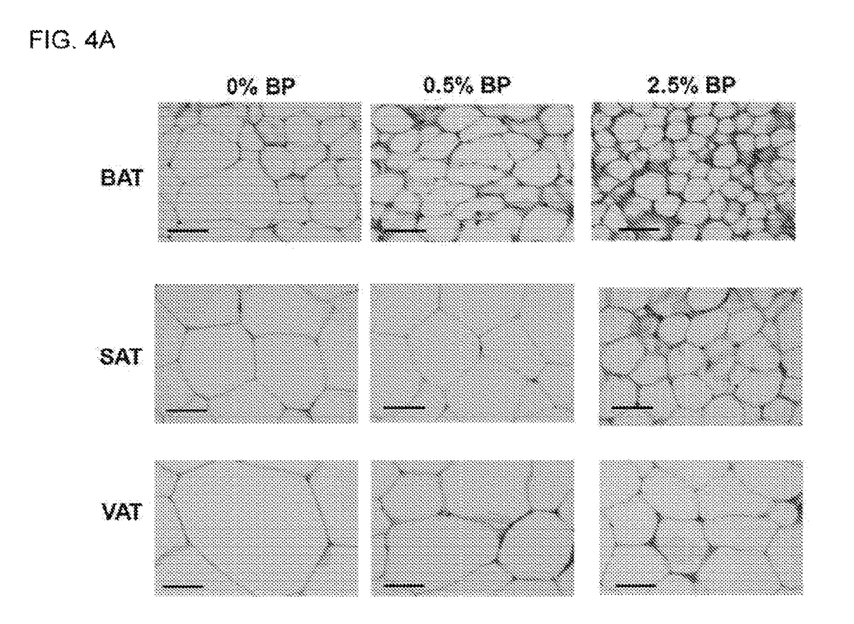
FIG. 4 shows morphological, cellular and biochemical changes in adipose tissues of male ob/ob mice fed *B. pilosa*. (A-C). Brown (BAT), subcutaneous (SAT) and visceral (VAT) adipose tissues of the ob/ob mice (FIG. 2) were collected. The adipose tissues were stained with hematoxylin and eosin (A). The size distribution (B) and average area (C) of adipocytes in every 100-mm$^2$ area range of adipose tissues were quantified using ImageJ software. The data, expressed as mean±SEM, was analyzed using Student's l-test. P<0.05 (*) are considered statistically significant. (D) Expression of PPAR-γ and C/EBPα in visceral adipose tissue (VAT) of the ob/ob mice (FIG. 2) fed with different doses of *B. pilosa* was analyzed with immunoblotting with the indicated antibodies.
Figure 4B:
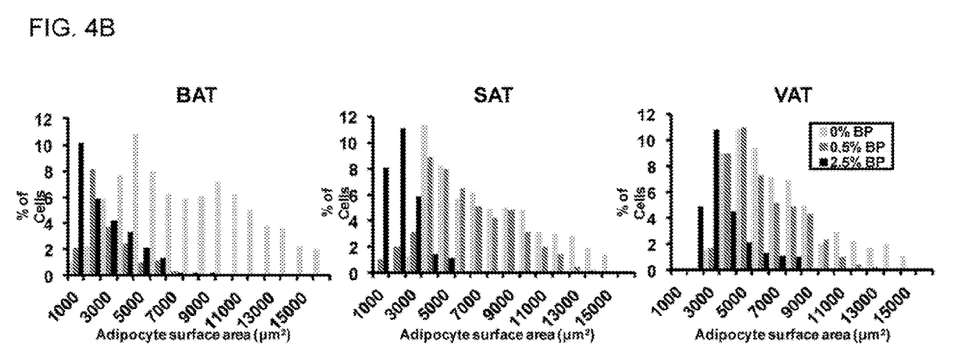
Figure 4C:
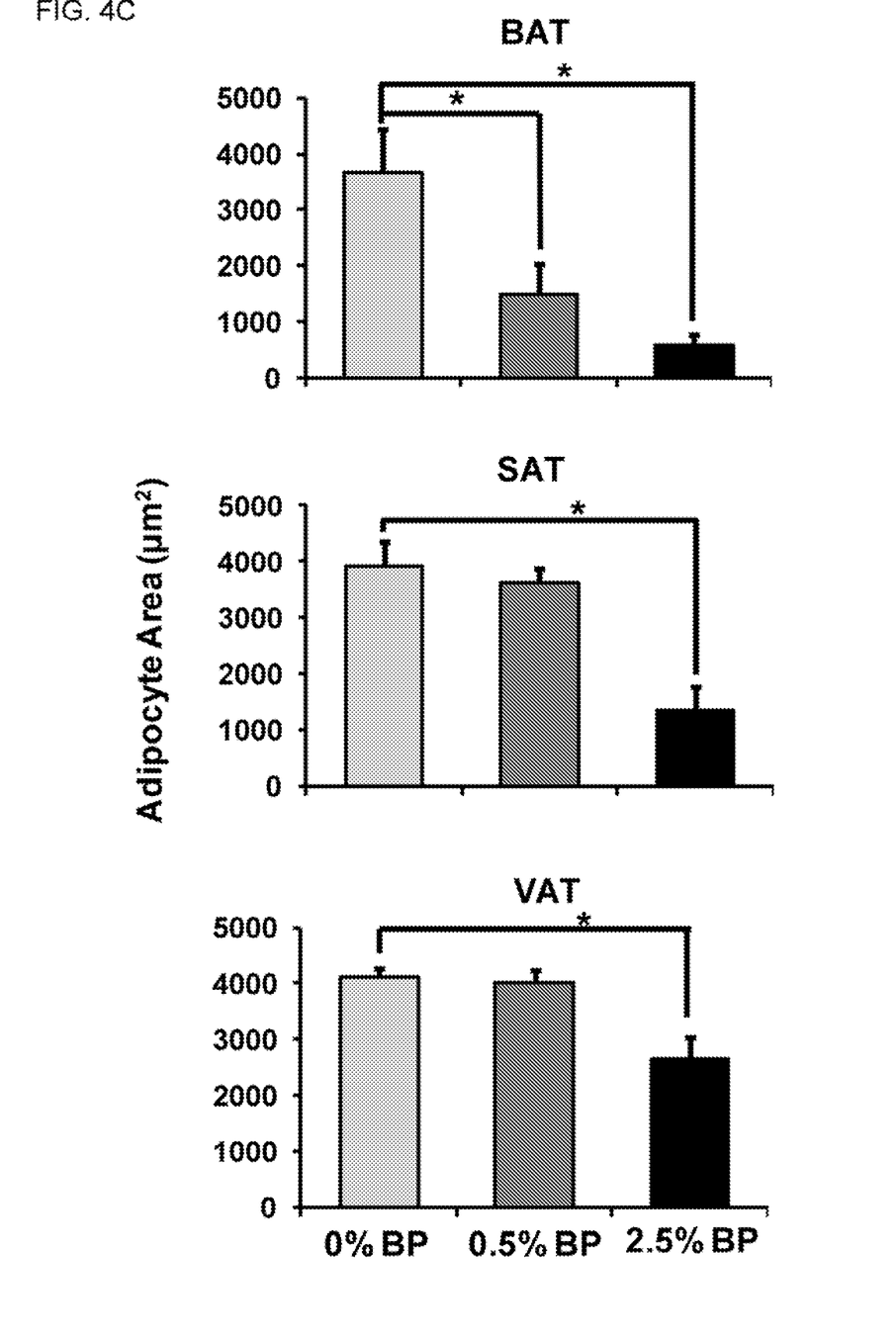

To dissect the mechanism by which *B. pilosa* decreased fat in mice, we examined the effect of *B. pilosa* on adipocytes in brown, subcutaneous and visceral adipose tissues. The histochemical data revealed that *B. pilosa* dose-dependently reduced cell size of adipocytes in all three types of adipose tissues (FIG. 4A). The cell size distribution of these adipose tissues was quantified. A shift from large cell size to small cell size in adipose tissues was observed in *B. pilosa*-fed mice (FIG. 4B). This shift was dependent on the dose of *B. pilosa* and more obvious in brown fat (FIG. 4B). Accordingly, *B. pilosa* dose-dependently diminished average adipocyte area in adipose tissues (FIG. 4C).

Figure 4D:
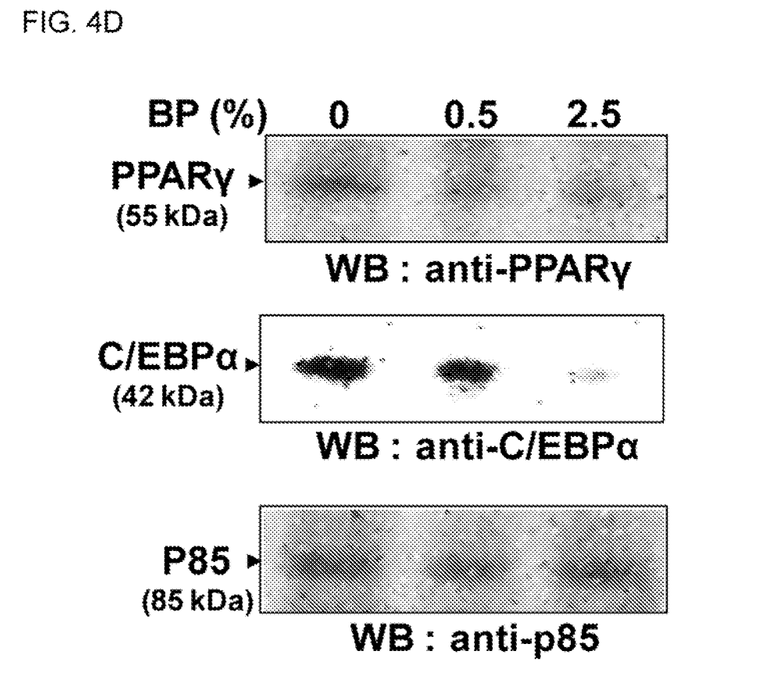

Because *B. pilosa* effectively reduced fat accumulation and fat cell size, we investigated which of the master gene(s) involved in adipogenesis and lipid metabolism were regulated by *B. pilosa*. We examined the impact of *B. pilosa* on the expression level of PPARγ and C/EBPα in the fat tissue of control and *B. pilosa*-fed mice. The data demonstrated that *B. pilosa* suppressed the expression of PPARγ and C/EBPα in a dose-dependent fashion (FIG. 4D).

Cytopiloyne Inhibits Adipogenesis but does not Affect Cell Viability in (Pre)Adipocytes.

Figure 5:
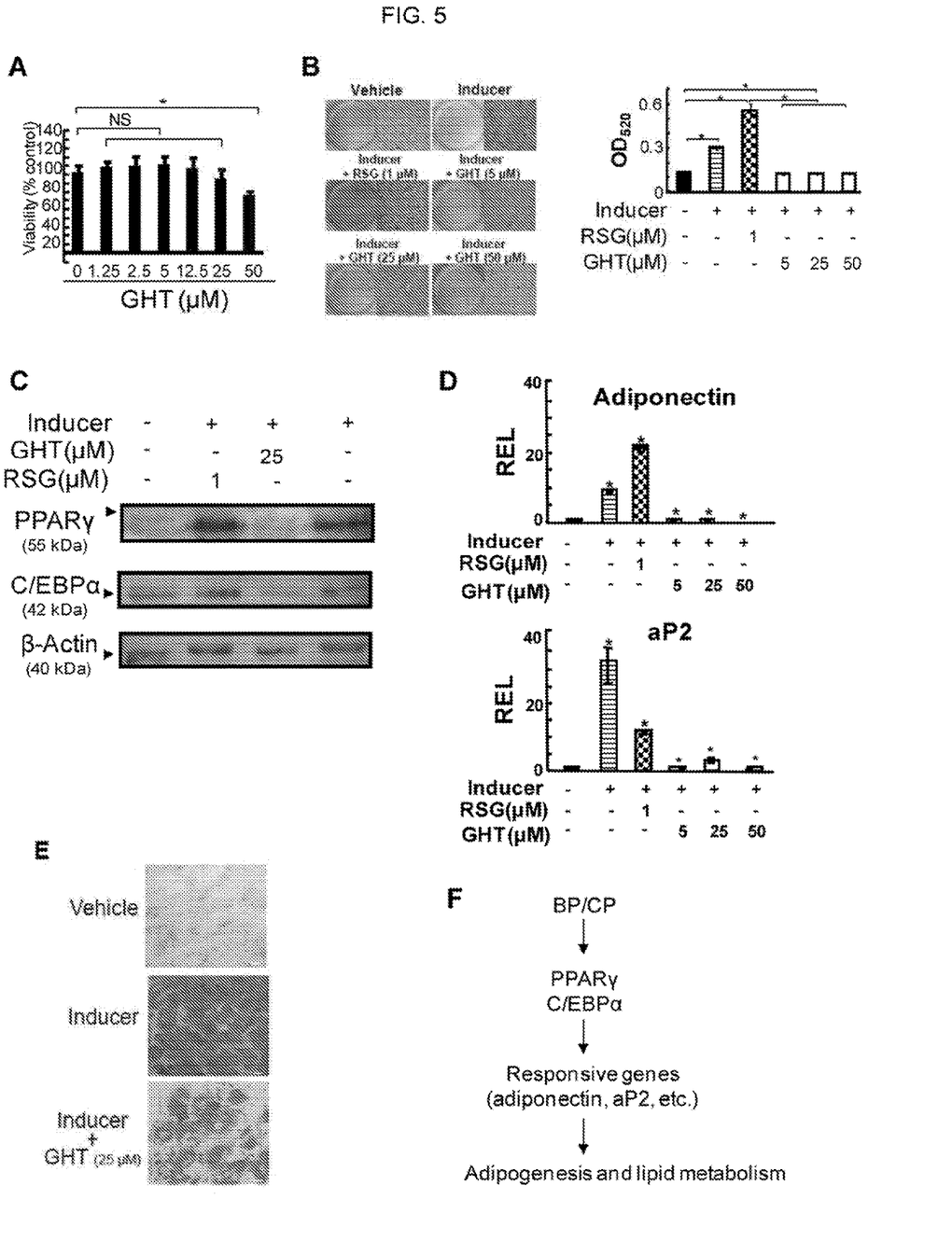

The average content of cytopiloyne in *B. pilosa* extract was used for quality control among *B. pilosa* extracts. The effect of cytopiloyne on adipogenesis in mouse 3T3-L1 pre-adipocytes was investigated. cytopiloyne at 25 µM or less did not show cytotoxicity and a slight cytotoxicity was observed in cytopiloyne at 50 µM (FIG. 5A). The effect of cytopiloyne on the differentiation of 3T3-L1 pre-adipocytes into adipocytes was investigated. As expected, the inducer composed of Dex, IBMX and insulin initiated the production of lipid droplets in adipocytes compared to control cells (Vehicle vs. Inducer, FIG. 5B). Rosiglitazone enhanced this production (Inducer+RSG, FIG. 5B). In sharp contrast, cytopiloyne dose-dependently inhibited this production (Inducer+cytopiloyne, FIG. 5B). The inhibitory effect of cytopiloyne on the production of lipid droplets was confirmed in human SGBS cells (FIG. 5E).

In parallel, the effect of cytopiloyne on PPARγ and C/EBPα in the same 3T3-L1 cells as in FIG. 5B was investigated. The 3T3-L1 pre-adipocytes had a basal expression level of PPARγ and C/EBPα (FIG. 5C). The inducer significantly up-regulated the expression level of both proteins. Further, rosiglitazone slightly increased this up-regulation (FIG. 5C). However, cytopiloyne abolished the up-regulation of PPARγ and C/EBPα expression by the inducer (FIG. 5C). The expression level of aP2 and adiponectin, two downstream genes of PPARγ and C/EBPα were examined. As expected, the inducer up-regulated the expression level of aP2 and adiponectin. In contrast, cytopiloyne abolished this up-regulation (FIG. 5D). The data showed that *B. pilosa* and its active constituent, cytopiloyne, reduced adipogenesis in adipocytes via down-regulation of PPARγ and C/EBPα genes and their downstream genes, aP2 and adiponectin (FIG. 5F).

We demonstrated that *B. pilosa* reduces fat content in mouse models. Its anti-obesity action involves the inhibition of PPARγ and C/EBPα pathways in adipose tissues. *B. pilosa* is recognized as safe for ethnomedicinal or culinary use worldwide. A dose of 400 mg *B. pilosa* extract per kilogram of body weight of three times per day, is considered safe in men. Here, mice did not show any toxicity to a daily dose of *B. pilosa* extract at 27 g per kg body weight (data not shown). Consistently, this did not affect biochemical parameters and number of blood cells except for blood glucose in rodents. Our data and other published literature suggest low safety risk of taking this plant orally. Aside from efficacy and palatability, *B. pilosa* is more cost-effective than *ginseng* and others due to its fast growth rate and low nutrient requirement.

We showed that *B. pilosa* and its active compound, cytopiloyne, inhibited adipogenesis in adipocytes. The mechanistic studies showed that *B. pilosa* and cytopiloyne suppressed the up-regulation of gene expression of PPARγ and C/EBPα and their downstream genes, aP2 and adiponectin, during adipogenesis. We also observed an increase in protein content in ICR mice and ob/ob mice. This observation might be due to the effect of *B. pilosa* on the energy shift from fat deposition to protein deposition since food intake did not show a significant difference in control and *B. pilosa*-fed animals. It has been shown that the energy required to deposit 1 kJ of protein and 1 kJ of fat was 2.25 and 1.36 kJ in Zucker rats, respectively. Therefore, unequal conversion between fat and protein in ob/ob mice by *B. pilosa* may explain the reduction in their body weight (Liang. Y.-C. et al. *Bidens pilosa* and its active compound inhibit adipogenesis and lipid accumulation via down-modulation of the C/EBP and PPARγ pathways. *Sci. Rep.* 6, 24285; doi: 10.1038/srep24285 (2016).

All references cited and discussed in this specification are incorporated herein by reference in their entireties and to the same extent as if each reference was individually incorporated by reference.

What is claimed is:

1. A method for reducing fat content and gaining muscle mass or muscle content of body composition in a non-diabetic subject in need thereof, comprising:
   administering to the non-diabetic subject in need thereof a composition comprising a therapeutically effective amount of *Bidens pilosa* extract, or an active compound isolated from the *Bidens pilosa* extract to reduce the fat content and gain the muscle mass or muscle content of the body composition in the subject in need thereof.

2. The method of claim 1, wherein the subject:
   is non-obese but in need of increasing the protein content of lean tissues.

3. The method as claim 1, wherein the subject:
   (i) does not have metabolic syndromes; or
   (ii) does not have hypertension.

4. The method of claim 1, wherein the subject is selected from the group consisting of humans, non-human mammals, birds, reptiles, fishes, and amphibians.

5. The method of claim 1, wherein the active compound is a polyacetylenic compound of formula (I):

wherein
   $R_1$ is H or CH3;
   $R_2$ is monosaccharide;
   $R_3$ is H or $COCH_2COOH$;
   m=3 or 4;
   n=0 or 1;
   o=1 or 2; and
   p=1 or 2.

6. The method of claim 1, wherein the *Bidens pilosa* extract is in a powder form.

7. The method of claim 1, wherein the composition is in the form of food, an animal feed material, or a medicine.

8. The method of claim 1, wherein the composition is in a dosage form selected from the group consisting of oral, capsule, suppository and parenteral.

9. The method of claim 1, wherein the medicament is at a dosage of no less than 0.001 mg/kg body weight of the subject in need thereof.

10. The method of claim 1, wherein the medicament is at a dosage of no less than 0.015 mg/kg body weight of the animal in need thereof.

11. The method of claim 1, wherein the active compound is cytopiloyne.

12. The method of claim 1, wherein the composition comprises an animal feed and 0.5%-15% (w/w) of *Bidens pilosa*.

13. The method of claim 1, which does not involve reducing food intake in the subject in need thereof.

14. A method for reducing fat content and gaining muscle mass or muscle content of body composition in a non-obese subject in need thereof, comprising:
  administering to the non-obese subject in need thereof a composition comprising a therapeutically effective amount of a polyacetylenic compound of formula (I) to reduce the fat content and gain the muscle mass or muscle content in the non-obese subject in need thereof:

wherein
  $R_1$ is H or CH3;
  $R_2$ is monosaccharide;
  $R_3$ is H or $COCH_2COOH$;
  m=3 or 4;
  n=0 or 1;
  o=1 or 2; and
  p=1 or 2.

15. The method of claim 14, wherein the polyacetylenic compound is selected from the group consisting of

A: $R = COCH_2COOH$
A': R = H

B: $R = COCH_2COOH$
B': R = H

C: $R = COCH_2COOH$
C': R = H

16. The method of claim 5, wherein the polyacetylenic compound is selected from the group consisting of

A: $R = COCH_2COOH$
A': R = H

B: $R = COCH_2COOH$
B': R = H

C: $R = COCH_2COOH$
C': R = H

17. The method of claim 2, wherein the active compound is cytopiloyne.

18. The method of claim 3, wherein the active compound is cytopiloyne.

19. The method of claim 9, wherein the active compound is cytopiloyne.

20. The method of claim 10, wherein the active compound is cytopiloyne.

* * * * *

UNITED STATES PATENT AND TRADEMARK OFFICE
CERTIFICATE OF CORRECTION

PATENT NO. : 10,632,165 B2  
APPLICATION NO. : 16/068125  
DATED : April 28, 2020  
INVENTOR(S) : Wen-Chin Yang, Lee-Tian Chang and Yu-Chuan Liang Page 1 of 1

It is certified that error appears in the above-identified patent and that said Letters Patent is hereby corrected as shown below:

In the Claims

Column 16, Line 62, delete "medicament" and insert -- composition --

Column 16, Line 65, delete "medicament" and insert -- composition --

Signed and Sealed this  
Thirtieth Day of June, 2020

Andrei Iancu  
*Director of the United States Patent and Trademark Office*